US010465127B2

(12) United States Patent
Sauge et al.

(10) Patent No.: US 10,465,127 B2
(45) Date of Patent: Nov. 5, 2019

(54) METHOD AND DEVICE FOR REDUCING HEAVY POLYCYCLIC AROMATIC COMPOUNDS IN HYDROCRACKING UNITS

(71) Applicant: AXENS, Rueil Malmaison (FR)

(72) Inventors: Thibault Sauge, Lyons (FR); Roberto Gonzalez Llamazares, Londres (GB); Jerome Bonnardot, Le Chesnay (FR); Jacinthe Frecon, Rueil-Malmaison (FR)

(73) Assignee: AXENS, Rueil Malmaison (FR)

( * ) Notice: Subject to any disclaimer, the term of this patent is extended or adjusted under 35 U.S.C. 154(b) by 0 days.

(21) Appl. No.: 15/538,234

(22) PCT Filed: Dec. 17, 2015

(86) PCT No.: PCT/EP2015/080220
§ 371 (c)(1),
(2) Date: Jun. 21, 2017

(87) PCT Pub. No.: WO2016/102301
PCT Pub. Date: Jun. 30, 2016

(65) Prior Publication Data
US 2017/0342331 A1     Nov. 30, 2017

(30) Foreign Application Priority Data

Dec. 22, 2014  (FR) ...................................... 14 63096

(51) Int. Cl.
*C10G 47/00*  (2006.01)
*C07C 7/04*  (2006.01)
(Continued)

(52) U.S. Cl.
CPC ................ *C10G 47/00* (2013.01); *C07C 5/10* (2013.01); *C07C 15/56* (2013.01); *C10G 7/00* (2013.01)

(58) Field of Classification Search
None
See application file for complete search history.

(56) References Cited

U.S. PATENT DOCUMENTS 2,934,492 A    4/1960  Hemminger
3,494,861 A    2/1970  Munro
(Continued)

FOREIGN PATENT DOCUMENTS

EP          665283 B1     3/2000

OTHER PUBLICATIONS

International Search Report PCT/EP2015/080220 dated Jul. 3, 2016.

*Primary Examiner* — Philip Y Louie
(74) *Attorney, Agent, or Firm* — Millen, White, Zelano and Branigan, P.C.

(57) ABSTRACT

The invention concerns a process and a facility for reducing the concentration of heavy polycyclic aromatic compounds (HPNA) in the recycle loop of hydrocracking units, which comprises a fractionation column.
In accordance with this process, a stream is withdrawn from the fractionation column at the level of at least one plate located between the supply plate and the plate for withdrawing the heaviest distillate fraction; the stream is stripped in an external stripping step by a stripping gas, in the presence of a portion of the residue. The separated gaseous effluent is recycled to the column, advantageously as a stripping gas, and the liquid fraction is recycled to the hydrocracking step; a residue is purged in the stripping step.

16 Claims, 2 Drawing Sheets

(51) Int. Cl.
*B01D 3/00* (2006.01)
*C10G 7/00* (2006.01)
*C07C 5/10* (2006.01)
*C07C 15/56* (2006.01)

(56) References Cited

U.S. PATENT DOCUMENTS

| | | |
|---|---|---|
| 3,655,551 A | 4/1972 | Hass |
| 2009/0065401 A1 | 3/2009 | Petri |
| 2013/0220885 A1* | 8/2013 | Low .................. C10G 47/00 208/85 |

* cited by examiner

METHOD AND DEVICE FOR REDUCING HEAVY POLYCYCLIC AROMATIC COMPOUNDS IN HYDROCRACKING UNITS

The invention relates to a process and a device for reducing the concentration of heavy polycyclic aromatic compounds (HPNA) in the recycle loop of hydrocracking units.

Hydrocracking processes are routinely used in refining to transform mixtures of hydrocarbons into products which can be upgraded easily. These processes may be used to transform light cuts such as gasolines, for example, into lighter cuts (LPG). However, they are more usually used to convert heavier feeds (such as oil cuts or heavy synthetics, for example gas oils obtained from vacuum distillation or effluents from a Fischer-Tropsch unit) into gasoline or naphtha, kerosene or gas oil. This type of process is also used to produce oils.

In order to increase the conversion of hydrocracking units, a portion of the unconverted feed is recycled, either to the reaction section through which it has already passed, or to an independent reaction section. This causes an unwanted accumulation in the recycle loop of polycyclic aromatic compounds formed in the reaction section during cracking reactions. These compounds poison the hydrocracking catalyst, which reduces the catalytic activity as well as the cycle time. They can also precipitate or be deposited in the cold parts of the unit, thus generating disruptions.

Thus, there is a need for improving the hydrocracking process in order to reduce the formation of polycyclic aromatic compounds or to eliminate them without reducing the yield of upgradable products.

HPNA compounds are defined as polycyclic or polynuclear aromatic compounds which thus comprise several condensed benzene nuclei or rings. They are usually known as HPA, Heavy Polynuclear Aromatics, or PNA or HPNA.

Typically, HPNAs known as heavies comprise at least 4 or even at least 6 benzene rings in each molecule. The compounds with fewer than 6 rings (pyrene derivatives, for example) can be hydrogenated more easily and are thus less likely to poison the catalysts. As a consequence, we are more particularly interested in compounds that are the most representative of families containing 6 aromatic rings or more such as, for example, coronene (a compound containing 24 carbon atoms), dibenzo(e,ghi) perylene (26 carbon atoms), naphtho[8,2,1,abc] coronene (30 carbon atoms) and ovalene (32 carbon atoms), which are the compounds which are the most easily identifiable and quantifiable, for example by chromatography.

The Applicant's U.S. Pat. No. 7,588,678 describes a hydrocracking process with a recycle of the unconverted 380° C.+ fraction, in which process the HPNA compounds are eliminated from the recycled fraction by means of an adsorbent. Other techniques for reducing the quantity or for eliminating the HPNA are described in the prior art for that patent such as, for example, their reduction via a hydrogenation or their precipitation followed by a filtration.

The U.S. Pat. No. 4,961,839 describes a hydrocracking process for increasing the conversion per pass using high flow rates of hydrogen in the reaction zone, by vaporizing a large proportion of the hydrocarbons sent to the column for separating the products and by concentrating the polycyclic aromatic compounds in a small heavy fraction which is extracted from that column. In that process, a heavy fraction is withdrawn from the level of a plate located above the supply point and below the point for withdrawing the gas oil distillate; that heavy fraction is recycled to the hydrocracker. The bottom of the column (residue) is recycled directly to the fractionation column That type of technique can indeed reduce the concentration of HPNA in the recycle loop to the reactor, but results in significant losses of yields and high costs linked to the quantities of hydrogen.

The patent applications WO 2012/052042 and WO 2012/052116 (corresponding to US-2013/0220885) describe a hydrocracking process in which the bottom of the fractionation column (residue) is stripped as a counter-current in a stripping column. The light fraction obtained after stripping is sent to the fractionation column and at least a portion of the heavy fraction obtained from stripping is purged, the other portion of that fraction optionally being recycled to the stripping column.

Those processes have brought about improvements in the reduction of HPNAs, but often to the detriment of the yields and costs.

The process of the invention can not only be used to concentrate the polycyclic aromatic hydrocarbons in the unconverted fractions (residues) in order to eliminate them and reduce the quantity of residue purged in order to increase the conversion, but also be used to improve the yield of upgradable products (for example by preventing over-cracking of gas oil) and/or the catalytic cycle time compared with prior art processes. The invention also has the advantage of considerably reducing the quantity of HPNA containing at least 6 aromatic rings presented to the hydrocracker and which are the most refractory to the reactions occurring during hydrocracking.

The process in accordance with the invention is based on positioning a side stream above the supply to the column, and below the withdrawal for the heaviest gas oil distillate, and stripping the withdrawn fraction then returning all or a portion of the separated gaseous effluent to the column, preferably as the stripping gas. This results in super-evaporation. The separation is carried out by combining the fractionation column with a stripper which strips said withdrawn fraction. This stripper also receives a portion of the residue which has been stripped. Thus, the purge is carried out at the level of the stripper.

This process also has the advantage of not introducing an excess of gas into the column by injecting a stripping gas external to the process (for example steam). Another advantage is to advance upgrading of the products even further, by treatment of the residue during stripping, this residue being considered to be a waste in the prior art (purge).

More precisely, the invention concerns a process for hydrocracking an oil feed comprising at least 10% by volume of compounds boiling above 340° C., comprising a hydrocracking step, optionally followed by a separation of the gases from the hydrocracked effluent, then a step for fractionation of said effluent, which separates at least one distillate and a residue, a portion of said residue being recycled to the hydrocracking step, said fractionation step comprising a distillation in a column provided with plates, in which column:

said at least partially vaporized effluent supplies the column over a supply plate, said distillate is withdrawn from the level of a withdrawal plate, said residue is evacuated at an evacuation point, and a stripping gas is injected at an injection point located below the supply plate, in which process a portion of the stream present at the level of at least one plate located between the supply plate and the plate for withdrawing the heaviest distillate fraction is withdrawn from the column, all or a portion, preferably all, of said withdrawn stream is stripped in an external stripping step by a stripping gas, in the presence of a portion of the residue evacuated from the column, and a gaseous effluent and a liquid fraction are obtained, and all or a portion, preferably all, of the separated gaseous effluent is recycled to the column, and all or a portion, preferably all, of said liquid fraction is recycled to the hydrocracking step, and a residue is purged in the stripping step.

Advantageously, a portion of the stream present at the level of a plate close to the supply plate and located above it is withdrawn from the column, and preferably at the level of the plate which is closest to the supply plate.

Said withdrawn stream has a concentration of HPNA of less than 500 ppm by weight, preferably less than 350 ppm by weight and highly preferably less than 200 ppm by weight. It usually has a proportion of at least 70% by weight of unconverted hydrocarbons, preferably at least 80% by weight of unconverted hydrocarbons and highly preferably at least 90% by weight of unconverted hydrocarbons.

Advantageously, all or a portion, preferably all, of the gaseous effluent is recycled to the column below the supply plate.

Highly preferably, all or a portion, preferably all, of the gaseous effluent is recycled to the column as the stripping gas, and preferably as the only stripping gas. If necessary, it may be used with another stripping gas.

In accordance with the invention, all or a portion, preferably all, of the liquid effluent separated in said stripping step is recycled, preferably directly, to the hydrocracking step.

Preferably, a portion of the residue evacuated from the column is recycled to the hydrocracking step.

Preferably, the process operates in the presence of a stripping gas injected into the fractionation step. Preferably, it is steam, preferably at a pressure in the range 0.2 to 1.5 MPa.

The stripping gas injected into the external stripping step is preferably steam, preferably at a pressure in the range 0.2 to 1.5 MPa.

The hydrocracking step is carried out in conventional manner at a temperature of more than 200° C., a pressure of more than 1 MPa, a space velocity of 0.1 to 20 $h^{-1}$, and the $H_2$/hydrocarbons volume ratio is 80 to 5000 NL/L.

The invention also concerns a facility which comprises:
a hydrocracking section 2 provided with an inlet line 1 for the feed and an inlet line 8 for hydrogen,
optionally followed by a zone 4 for separating effluent in order to separate a gaseous fraction,
followed by a fractionation section 12 comprising at least one distillation column provided with plates, said column comprising:
at least one line 11 for the inflow of at least partially vaporized hydrocracked effluent onto at least one supply plate,
at least one line 14 for withdrawing at least one distillate from the level of a withdrawal plate,
at least one line 15a for evacuating residue,
and comprising at least one line 19 for injecting a stripping gas, the injection point being located below the supply plate,
the facility further comprising:
at least one line 20 for withdrawing a portion of the stream present at the level of at least one plate located between said supply plate and the plate for withdrawing the heaviest distillate fraction,
a stripper 25 external to the column, provided with an inlet line 20 for said withdrawn stream, a line 16 for introducing a portion of the residue evacuated from the column, a line 26 for injecting stripping gas, an outlet line 22 for the gaseous effluent, and an outlet line 27 for the liquid fraction,
and a line 22 for recycling all or a portion, preferably all, of said gaseous effluent to said column,
a line 27 for recycling all or a portion, preferably all, of said liquid fraction to the hydrocracking step,
a line 24 for purging a portion of the residue.

Advantageously, the withdrawal plate 20 is at the level of the plate closest to the supply plate.

Preferably, the lines 22 and 19 are merged, the gaseous effluent being the stripping gas; the line 22 supplies the gaseous effluent to the column at the stripping gas injection point (line 19).

Preferably, the facility further comprises at least one line 23, 18 for recycling a portion of the residue evacuated from the column to the hydrocracking step.

In a preferred disposition, there is no line for recycling a liquid fraction (line 27) separated in the stripping step to the fractionation column.

The invention will be better understood from the following description of the figures.

In the text, feeds are defined by their T5 boiling point (as will be explained below). The conversion of the feed is defined with respect to the cut point of the residue. The unconverted fraction is termed residue. The converted fraction comprises the fractions sought by the refiner (objectives).

The purged portion refers to a portion which leaves the process.

BRIEF DESCRIPTION OF THE DRAWINGS

The invention will be better understood from the following description of the figures.

FIG. 2 will be understood in combination with FIG. 1, and more precisely with the essential elements of FIG. 1 cited in the claims.

FIG. 1 presents a flowchart for a prior art hydrocracking process. To facilitate reading, the description of the conditions employed has been moved to a further part of the text below.

Figure 1:
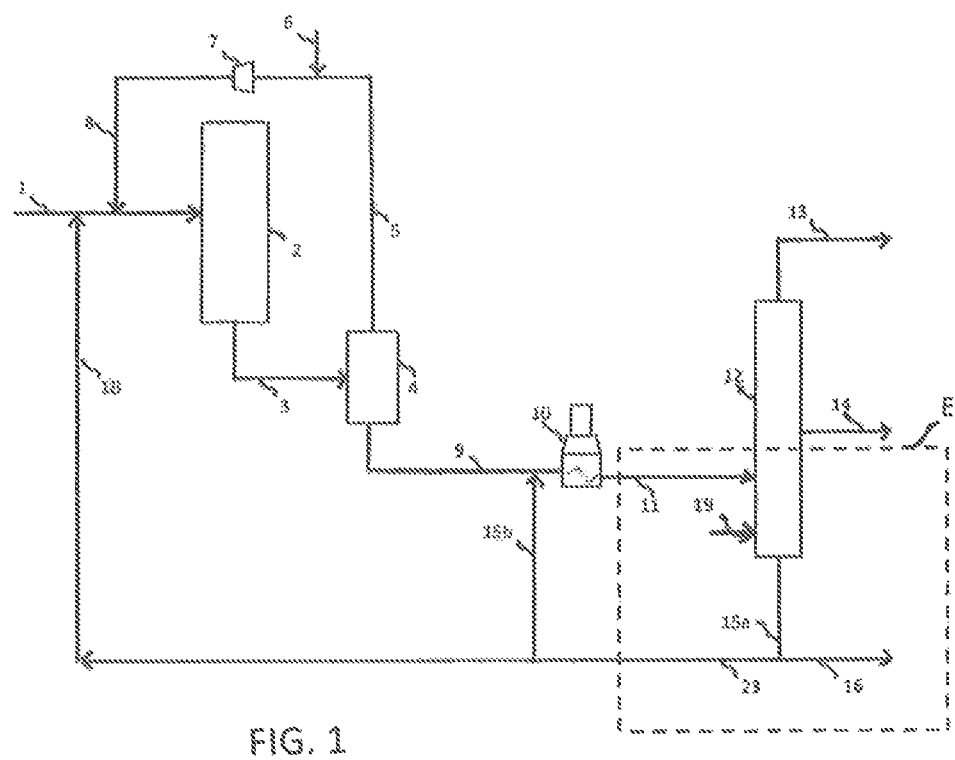
FIG. 1 represents the prior art.

The feed (line 1) composed of hydrocarbons of oil origin and/or synthetic hydrocarbons with a mineral or biological source is mixed with hydrogen supplied via the lines 5 (recycle) and/or 6 (makeup hydrogen) via the compressor 7 and the line 8.

The feed/hydrogen mixture thus formed is sent to the hydrocracking section 2. This section comprises one or more fixed bed or ebullated bed reactors.

When the hydrocracking section comprises one or more fixed bed reactors, each reactor may comprise one or more beds of catalyst carrying out hydrocracking of the hydrocarbons of the feed to form lighter hydrocarbons.

When the hydrocracking section comprises one or more ebullated bed reactors, a stream comprising liquid, solid and gas moves vertically through a reactor containing a bed of catalyst. The catalyst in the bed is maintained in a random motion in the liquid. The gross volume of the catalyst dispersed through the liquid is thus larger than the volume of catalyst when stopped. This technology has been widely described in the literature.

A mixture of liquid hydrocarbon and hydrogen is passed through the bed of particles of catalyst at a velocity such that the particles are caused to move in a random manner and thus become suspended in the liquid. Expansion of the catalytic bed in the liquid phase is controlled by the flow rate of recycle liquid in a manner such that in the equilibrium state, the major portion of catalyst does not go above a defined level in the reactor. The catalysts are in the form of extrudates or beads, preferably with a diameter in the range 0.8 mm to 6.5 mm in diameter.

In an ebullated bed process, large quantities of hydrogen gas and light hydrocarbon vapours rise through the reaction zone then in a zone which is free of catalyst. A portion of the liquid from the catalytic zone is recycled to the bottom of the reactor after separating a gaseous fraction and a portion is withdrawn from the reactor as product, usually at the top portion of the reactor.

The reactors used in an ebullated bed process are generally designed with a central vertical recycling conduit which acts as a flow tube for recycling liquid from the catalyst-free zone located above the ebullated bed of catalyst, via a recycling pump which can be used to recycle the liquid in the catalytic zone. Recycling the liquid means that both a uniform temperature can be maintained in the reactor and that the bed of catalyst can be kept in suspension.

The hydrocracking section may be preceded by or include one or more beds of hydrotreatment catalyst(s).

The effluent from the hydrocracking section 2 is sent via line 3 to a separation zone 4 in order to recover a gaseous fraction 5 on the one hand, along with a liquid fraction 9. The gaseous fraction 5 contains excess hydrogen which has not reacted in the reaction section 2. It is generally combined with fresh hydrogen arriving via the line 6 in order to be recycled as indicated below.

The liquid fraction 9 is reheated by any means 10, for example a furnace which could be associated with an exchanger (not shown), in order to at least partially vaporize it before supplying the fractionation section 12 via the line 11.

The fractionation section 12 comprises one or more distillation columns equipped with plates and contact means in order to separate various upgradable cuts (distillates) which are withdrawn by means of the lines 13 and 14, plus other optional side streams. These cuts have boiling point ranges situated, for example, in the gasoline, kerosene and gas oil ranges.

A heavier unconverted fraction (residue) is recovered from the bottom of the column (line 15a).

Stripping gas may be injected via the line 19. This line is located between the plate for supplying hydrocracked effluent (line 11) and the residue evacuation point (line 15a).

A portion of the residue may be purged via the line 16, with another portion recycled to the hydrocracking section via the lines 23 and 18 and another portion recycled to the fractionation section (line 15b).

In accordance with FIG. 1, a portion (line 15b) of the residue from the line 15a is mixed with the supply (line 9) upstream of the furnace 10 of the fractionation section and recycled as a mixture towards the fractionation section (line 11).

The purge 16 can in particular be used to eliminate at least a portion of the HPNA compounds which could accumulate in the recycle loop without this purge.

The zone E outlined in FIG. 1 defines the portion modified by the subject matter of the present invention.

Figure 2:
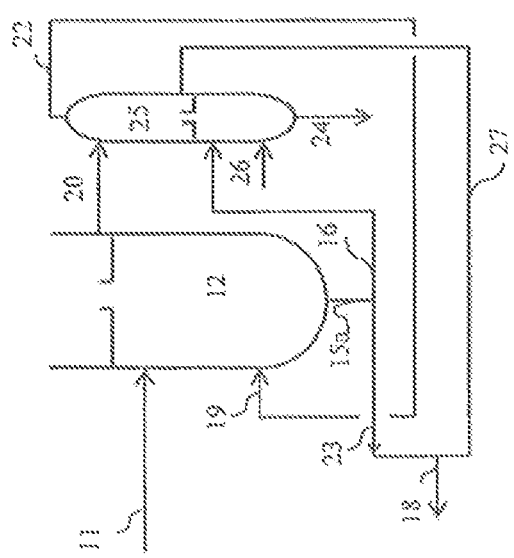
FIG. 2 illustrates the invention.

FIG. 2 presents the invention. The elements described above will not be described again here. It should be noted that the line 15b (recycle of residue to the fractionation column) is preferably dispensed with in the invention.

The fractionation section 12 comprises a single fractionation column. However, the invention could be implemented with several fractionation columns and at least one column would then comprise a zone E in accordance with the invention.

The liquid fraction 11 (hydrocracked effluent) which has previously been at least partially vaporized is supplied to the fractionation section 12.

A side stream (line 20) is positioned at the level of one of the plates of the column. It is possible to position one or more side streams at the level of the column Thus, a portion of the stream present at the level of at least one plate located between the plate for supplying effluent and the plate for withdrawing the heaviest distillate fraction is withdrawn.

This side stream (line 20) is preferably close to the supply plate. Preferably, a portion of the stream present at the level of the plate closest to the supply plate is withdrawn from the column.

The side stream (line 20) is positioned in a manner such that the withdrawn stream has a low concentration of HPNA of less than 500 ppm by weight, preferably less than 350 ppm by weight and highly preferably less than 200 ppm by weight, and most often, a large proportion of unconverted hydrocarbons in the hydrocracking section of at least 70% by weight of unconverted hydrocarbons, preferably at least 80% by weight of unconverted hydrocarbons and highly preferably at least 90% by weight of unconverted hydrocarbons.

In order to satisfy these criteria, the side stream (line 20) is preferably positioned above the supply plate, and preferably at the level of the plate closest to the supply plate.

The withdrawn stream (line 20) is introduced to the level of a plate in the external stripper 25. It is stripped in a step known as an external stripping step using a stripping gas (supplied via the line 26). All or a portion of the separated gaseous effluent is recycled to the column; in accordance with FIG. 2, all of the gaseous effluent is recycled.

The gaseous effluent (in its entirety in accordance with FIG. 2) is recycled (line 22) to the column below the plate from which the stream has been withdrawn and below the hydrocracked effluent supply plate.

Particularly advantageously, the recycled gaseous effluent is used as a stripping gas in the column Thus, it enters the column (line 19) at the injection point for the stripping gas. The injection point is located below the supply plate and above the residue evacuation point. It is preferably close to the point for evacuating residue at the column bottom.

Preferably, said recycled gaseous effluent is used as the only stripping gas; however, another stripping gas may be supplied if necessary.

This other stripping gas injected into the column (line 19) is advantageously steam, preferably low pressure steam, preferably at a pressure in the range 0.2 to 1.5 MPa.

A portion of the residue evacuated from the fractionation column (line 15a) is also introduced (line 16) into the external structure step (stripper 25). This introduction is carried out at the level of a plate which is located below the plate for introducing the stream withdrawn from the fractionation column.

Advantageously, the residue purge is carried out at the level of the stripping step (line 24); thus, preferably, no residue is purged from the fractionation column.

All or a portion of the liquid effluent (line 27) is recycled directly to the hydrocracking step. This effluent is removed in the stripper 25 at the level of a plate located between the plate for introducing withdrawn stream (supplied via line 20) and the plate for introducing residue (supplied via line 16). In accordance with FIG. 2, all of the liquid effluent (line 27) is mixed with the recycled residue portion (line 23) and the mixture is recycled (line 18) to the hydrocracking step.

Said lateral stripper 25 functions with injection of a stripping gas (line 26). This gas is preferably steam, preferably low pressure steam, preferably at a pressure in the range 0.2 to 1.5 MPa.

Description of the Conditions for the Hydrocracking, 2, and Separation Steps

This description refers to conventional implementational conditions which can be applied both to FIG. 1 (prior art) and to the invention (FIG. 2).

Feeds:

A wide variety of feeds may be treated in hydrocracking processes. In general, they contain at least 10% by volume, generally at least 20% by volume and often at least 80% by volume of compounds boiling above 340° C.

The feed may, for example, be LCO (light cycle oil—light gas oils obtained from a catalytic cracking unit), atmospheric distillates, vacuum distillates, for example gas oils obtained from straight run distillation of crude or from conversion units such as FCC, coking or visbreaking, as well as feeds originating from units for the extraction of aromatics from lubricating oil bases or obtained from solvent dewaxing of lubricating base oils, or in fact from distillates originating from processes for fixed bed or ebullated bed hydroconversion or desulphurization of AR (atmospheric residues) and/or VR (vacuum residues) and/or deasphalted oils, or the feed may in fact be a deasphalted oil, effluents from a Fischer-Tropsch unit or in fact any mixture of the feeds cited above. The above list is not limiting.

In general, the feeds have a T5 boiling point of more than 150° C. (i.e. 95% of the compounds present in the feed have a boiling point of more than 150° C.). In the case of gas oil, the T5 point is generally approximately 150° C. In the case of VGO, the T5 is generally more than 340° C., or even more than 370° C. The feeds which may be used thus fall within a wide range of boiling points. This range generally extends from gas oil to VGO, encompassing all possible mixtures with other feeds, for example LCO.

The nitrogen content of the feeds treated in the hydrocracking processes is usually more than 500 ppm by weight, generally in the range 500 to 10000 ppm by weight, more generally in the range 700 to 4500 ppm by weight and still more generally in the range 800 to 4500 ppm by weight.

The sulphur content in the feeds treated in the hydrocracking processes is usually in the range 0.01% to 5% by weight, generally in the range 0.2% to 4% by weight and yet more generally in the range 0.5% to 3% by weight. The feed may optionally contain metals. The cumulative nickel and vanadium content in the feeds treated in hydrocracking processes is preferably less than 10 ppm by weight, preferably less than 5 ppm by weight and yet more preferably less than 2 ppm by weight. The asphaltenes content is generally less than 3000 ppm by weight, preferably less than 1000 ppm by weight, and yet more preferably less than 300 ppm by weight.

Guard Beds

In the case in which the feed contains compounds of the resins and/or asphaltenes type, it is advantageous to initially pass the feed over a bed of catalyst or adsorbent which differs from the hydrocracking or hydrotreatment catalyst. The catalysts or guard beds used are in the shape of spheres or extrudates. Any other shape may be used. Particular possible shapes which may be used are included in the following non-limiting list: hollow cylinders, hollow rings, Raschig rings, toothed hollow cylinders, crenelated hollow cylinders, wheels known as pentarings, multiple-holed cylinders, etc.

These catalysts may have been impregnated with a phase which may or may not be active. Preferably, the catalysts are impregnated with a hydrodehydrogenating phase. Highly preferably, the CoMo or NiMo phase is used. These catalysts may have a macroporosity.

Operating Conditions:

The operating conditions such as temperature, pressure, hydrogen recycle ratio, or hourly space velocity may vary widely as a function of the nature of the feed, the quality of the desired products and the facilities available to the refiner. The hydrocracking/hydroconversion catalyst or hydrotreatment catalyst is generally brought into contact with the feeds described above in the presence of hydrogen, at a temperature of more than 200° C., often in the range 250° C. to 480° C., advantageously in the range 320° C. to 450° C., preferably in the range 330° C. to 435° C., at a pressure of more than 1 MPa, often in the range 2 to 25 MPa, preferably in the range 3 to 20 MPa, the space velocity being in the range 0.1 to 20 $h^{-1}$ preferably in the range 0.1 to 6 $h^{-1}$ and more preferably in the range 0.2 to 3 $h^{-1}$ and the quantity of hydrogen introduced being such that the volume ratio in liters of hydrogen/liters of hydrocarbon is in the range 80 to 5000 L/L, usually in the range 100 to 3000 L/L.

These operating conditions used in the hydrocracking processes can generally be used to obtain conversions per pass into converted products (i.e. with boiling points below the residue cut point) of more than 15%, and more preferably in the range 20% to 95%.

The Principal Aims:

The invention may be used in all hydrocrackers, namely:
the maxi-naphtha hydrocracker with a residue cut point which is generally between 150° C. and 190° C., preferably between 160° C. and 190° C., and usually 170° C.–180° C.,
the maxi-kerosene hydrocracker with a residue cut point which is generally between 240° C. and 290° C., and usually 260° C.–280° C.,
the maxi-gas oil hydrocracker with a residue cut point which is generally between 340° C. and 385° C., and usually 360° C.–380° C.

EMBODIMENTS

The hydrocracking/hydroconversion processes using the catalysts in accordance with the invention cover the ranges of pressure and conversion from mild hydrocracking to high pressure hydrocracking.

The term "mild hydrocracking" means hydrocracking resulting in moderate conversions, generally below 40%, and operating at low pressures, generally between 2 MPa and 9 MPa. The hydrocracking catalyst may be used alone, in a single or in more fixed bed catalytic beds, in one or more reactors, in a "once-through" hydrocracking layout, with or without liquid recycling of the unconverted fraction, optionally in association with a hydrorefining catalyst located upstream of the hydrocracking catalyst.

The hydrocracking may be operated at high pressure (at least 10 MPa).

In a first variation, the hydrocracking may be operated in accordance with a hydrocracking layout which is known as a "two-step" layout, with intermediate separation between the two reaction zones; in a given step, the hydrocracking catalyst may be used in one or in both reactors associated or otherwise with a hydrorefining catalyst located upstream of the hydrocracking catalyst.

In a second variation, what is known as "once-through" hydrocracking may be carried out. This variation generally initially comprises intense hydrorefining which is intended to carry out intense hydrodenitrogenation and hydrodesulphurization of the feed before it is sent to the hydrocracking catalyst proper, in particular in the case in which it comprises a zeolite. This intense hydrorefining of the feed brings about only a limited conversion of this feed into lighter fractions. The conversion, which is still insufficient, must therefore be supplemented on the more active hydrocracking catalyst.

The hydrocracking section may contain one or more beds of identical or different catalysts. When the preferred products are middle distillates, basic amorphous solids are used, for example alumina or silica-aluminas or basic zeolites, optionally supplemented with at least one hydrogenating metal from group VIII and preferably also supplemented with at least one metal from group VIB. These basic zeolites are composed of silica, alumina and one or more exchangeable cations such as sodium, magnesium, calcium or rare earths.

When gasoline is the major desired product, the catalyst is generally composed of a crystalline zeolite onto which small quantities of a metal from group VIII are deposited, and also, more preferably, a metal from group VIB.

The zeolites which may be used are natural or synthetic and may, for example, be selected from X, Y or L zeolites, faujasite, mordenite, erionite or chabasite.

Hydrocracking may be carried out in just one or in more ebullated bed reactors, with or without a liquid recycle of the unconverted fraction, optionally in association with a hydrorefining catalyst located in a fixed bed or ebullated bed reactor upstream of the hydrocracking catalyst. The ebullated bed is operated with withdrawal of spent catalyst and the daily addition of fresh catalyst in order to keep the catalyst activity stable.

Liquid/Gas Separation (4):

The separator 4 separates the liquid and gas present in the effluent leaving the hydrocracking unit. Any type of separator that can carry out this separation may be used, for example a flash drum, a stripper, or even a simple distillation column Fractionation (12):

The fractionation section is generally constituted by one or more columns comprising a plurality of plates and/or internal packing which may preferably be operated in counter-current mode. These columns are usually steam stripped and include a reboiler in order to facilitate vaporization. It can be used to separate hydrogen sulphide ($H_2S$) and light components (methane, ethane, propane, butane etc) from the effluents, as well as the hydrocarbon cuts with boiling points in the gasoline, kerosene and gas oil ranges along with a heavy fraction recovered from the bottom of the column, all or a portion of which may be recycled to the hydrocracking section.

EXAMPLES

Example 1: Prior Art

This example is based on the configuration of FIG. 1. Two samples from an operating industrial unit based on the configuration of FIG. 1 were analysed. The properties are recorded in Table 1 below.

It should be noted that because of the configuration, the streams 15a, 16, 18 and 23 had exactly the same properties.

The fractionation of stream 11 in the column 12 was computer simulated using the PRO/II version 8.3.3 software marketed by SimSci. The physical and analytical properties of the resulting streams were simulated and compared with the physical and analytical properties of actual samples.

The operating conditions for the column used for the simulation are recorded in Table 2 below.

TABLE 1

Properties of the streams of the layout of FIG. 1

| Configuration | | Streams from FIG. 1 | | | |
|---|---|---|---|---|---|
| Stream number | | 11 | 15a | 18 | 16 |
| Yield | % by wt | 100 | 42 | 39.5 | 2.5 |
| Quantity of gas oil in stream | % by wt | 64.0 | 10.9 | 10.9 | 10.9 |
| Specific gravity | | 0.805 | 0.828 | 0.828 | 0.828 |
| HPNA | | | | | |
| Coronene | ppm by wt | 209 | 497 | 497 | 497 |
| Dibenzo(e,ghi)perylene | ppm by wt | 33 | 78 | 78 | 78 |
| Naphtho[8,2,1 abc] coronene | ppm by wt | 81 | 192 | 192 | 192 |
| Ovalene | ppm by wt | 57 | 135 | 135 | 135 |
| Total HPNA | ppm by wt | 378 | 902 | 902 | 902 |
| TBP, % by wt | | | | | |
| Initial boiling point | °C. | 128 | 200 | 200 | 200 |
| 10% | °C. | 200 | 368 | 368 | 368 |
| 50% | °C. | 326 | 402 | 402 | 402 |
| 90% | °C. | 440 | 477 | 477 | 477 |
| Final boiling point | °C. | 524 | 524 | 524 | 524 |

1: Specific gravity SG = $\rho_{sample}$ at 20° C./$\rho_{H2O}$ at 4° C., where $\rho$ is the density expressed in g/cm$^3$

TABLE 2

Operating conditions for the column

| Operating conditions for fractionation | | FIG. 1 |
|---|---|---|
| Pressure, top of column | barg | 1.0 |
| Pressure, bottom of column | barg | 1.5 |
| Temperature, inlet feed | °C. | 377 |
| Number of theoretical plates | | 34 |
| Flow rate of stripping steam | kg of steam/tonne of feed | 17 |

Starting from the properties of the stream 11 entering the fractionation column (see Table 1), the PRO/II simulation was able to establish the properties of the stream 15 leaving the fractionation column; in particular, the HPNA distribution could be modelled.

Based on these results, the configurations of the invention were simulated. The results are disclosed below for the configuration in accordance with the invention.

Example 2: Configuration of FIG. 2 (in Accordance with the Invention)

Table 3 below provides the characteristics of the streams 11, 18 and 24 in the configuration of FIG. 2 obtained from the PRO/II simulation. The operating conditions used for the simulation are recorded in Table 4.

TABLE 3

Properties of the streams of the layout of FIG. 2

| | Streams from FIG. 2e | | |
|---|---|---|---|
| Configuration Stream number | 11 inlet | 18 liquid recycle | 24 purge |
| Yield | 100 | 39.5 | 2.5 |
| Quantity of gas oil in stream | 64.0 | 6.1 | 3.3 |
| Specific gravity | 0.805 | 0.8285 | 0.8337 |
| HPNA | | | |
| Coronene | 209 | 378 | 2954 |
| Dibenzo(e,ghi)perylene | 33 | 93 | 430 |
| Naphtho[8,2,1 abc] coronene | 81 | 91 | 1197 |
| Ovalene | 57 | 52 | 853 |
| Total HPNA | 378 | 613 | 5435 |
| TBP, % by wt | | | |
| Initial boiling point | 128 | 117 | 327 |
| 10% | 200 | 391 | 390 |
| 50% | 326 | 410 | 441 |
| 90% | 440 | 474 | 514 |
| Final boiling point | 524 | 524 | 524 |

1: Specific gravity SG = $\rho_{sample}$ at 20° C./$\rho_{H2O}$ at 4° C., where $\rho$ is the density expressed in g/cm$^3$

TABLE 4

Operating conditions for the column

| Operating conditions for fractionation | | |
|---|---|---|
| Pressure, top of column | Barg | 1.0 |
| Pressure, bottom of column | Barg | 1.5 |
| Temperature, inlet feed | ° C. | 377 |
| Number of theoretical plates | | 34 |
| Flow rate of stripping steam | kg of steam/tonne of feed | 17 |
| Operating conditions for side stripper | | |
| Pressure, top of column | Barg | 1.4 |
| Pressure, bottom of column | Barg | 1.5 |
| Number of theoretical plates | | 6 |
| Flow rate of stripping steam | kg of steam/tonne of feed | 28 |

Compared with the configuration of FIG. 1, the configuration of FIG. 2 can be used to maximize the quantity of HPNA (5435 ppm by weight compared with 902 ppm by weight in the configuration of FIG. 1) in the unconverted fraction which was purged via the line 24. At the same time, the quantity of HPNA was minimized in the stream which returns to the reaction section via the line 18 (613 ppm by weight compared with 902 ppm by weight in the configuration of FIG. 1), which reduced the quantity of HPNA by 32.0%.

In addition, the proportion of refractory and poisonous heavy HPNA (naphtho [8,2,1 abc] coronene+ovalene) compared with the total quantity of HPNA in the stream returning to the reaction section was much lower for the configuration of FIG. 2 (23.2%) than for the configuration of FIG. 1 (36.3%). This indicates that not only was there less total HPNA in the stream returning to the reaction section via the line 18, but also, the proportion of the refractory and poisonous heavy HPNA (naphtho [8,2,1 abc] coronene+ovalene) was lower.

In addition, this configuration could minimize the quantity of gas oil sent to the reaction section via the line 18 because the quantity of gas oil returned to the reaction section was only 6.1% by weight compared with 10.9% by weight in the configuration of FIG. 1.

The invention claimed is:

1. A process for hydrocracking an oil feed comprising at least 10% by volume of compounds boiling above 340° C., comprising a hydrocracking step, optionally followed by a separation of the gases from the hydrocracked effluent, then a step for fractionation of said effluent, which separates at least one distillate and a residue, a portion of said residue being recycled to the hydrocracking step, said fractionation step comprising a distillation in a column provided with plates, in which column:
   said at least partially vaporized effluent supplies the column over a supply plate,
   said distillate is withdrawn from the level of a withdrawal plate,
   said residue is evacuated at an evacuation point,
   and a stripping gas is injected at an injection point located below the supply plate, in which process
   a portion of the stream present at the level of at least one plate located between the supply plate and the plate for withdrawing the heaviest distillate fraction is withdrawn from the column,
   all or a portion of said withdrawn stream is stripped in an external stripping step by a stripping gas, in the presence of a portion of the residue evacuated from the column, and a gaseous effluent and a liquid fraction are obtained,
   all or a portion of the separated gaseous effluent is recycled to the column,
   all or a portion of said liquid fraction is removed at the level of a plate located between a plate introducing withdrawn steam and a plate introducing portion of the residue evacuated from the column, and recycled to the hydrocracking step,
   and a residue is purged in the stripping step.

2. The process as claimed in claim 1, in which a portion of the stream present at the level of a plate close to the supply plate and located above it is withdrawn from the column.

3. The process as claimed in claim 1, in which said withdrawn stream has a concentration of HPNA of less than 500 ppm by weight.

4. The process as claimed in claim 1, in which said withdrawn stream has a proportion of at least 70% by weight of unconverted hydrocarbons.

5. The process as claimed in claim 1, in which all or a portion of the gaseous effluent is recycled to the column below the supply plate.

6. The process as claimed in claim 1, in which the gaseous effluent is recycled to the column as the stripping gas.

7. The process as claimed in claim 1, in which all or a portion of the liquid effluent separated in said stripping step is recycled directly to the hydrocracking step.

8. The process as claimed in claim 1, in which the stripping gas injected into the external stripping step and optionally into the fractionation step is steam.

9. The process as claimed in claim 1, in which a portion of the residue evacuated from the column is recycled to the hydrocracking step.

10. The process according to claim 1, wherein introduction of the portion of the residue evacuated from the column in the external stripping step is done at a plate located below a plate introducing said withdrawn stream.

11. The process according to claim 1, wherein a portion of the stream present at the level of at least one plate located below the supply plate and above the plate withdrawing the heaviest distillate fraction is withdrawn from the column.

12. The process according to claim 1, wherein all of said withdrawn stream is stripped in an external stripping step by a stripping gas, all of the separated gaseous effluent is recycled to the column, and of said liquid fraction is removed at the level of a plate located between a plate introducing withdrawn steam and a plate introducing portion of the residue evacuated from the column, and recycled to the hydrocracking step.

13. The process according to claim 1, wherein a portion of the stream present at the level of the plate which is closest to the supply plate is withdrawn from the column.

14. The process as claimed in claim 1, in which said withdrawn stream has a concentration of HPNA of less than 350 ppm by weight.

15. The process as claimed in claim 1, in which said withdrawn stream has a proportion of at least 80% by weight of unconverted hydrocarbons.

16. The process as claimed in claim 1, in which all of the gaseous effluent is recycled to the column below the supply plate.

* * * * *